(12) United States Patent
Mori et al.

(10) Patent No.: US 8,838,201 B2
(45) Date of Patent: Sep. 16, 2014

(54) ATLAS-BASED ANALYSIS FOR IMAGE-BASED ANATOMIC AND FUNCTIONAL DATA OF ORGANISM

(75) Inventors: Susumu Mori, Ellicott City, MD (US); Andreia V. Faria, Columbia, MD (US); Michael I. Miller, Towson, MD (US); Kenichi Oishi, Lutherville Timonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/703,859

(22) PCT Filed: Jun. 22, 2011

(86) PCT No.: PCT/US2011/041488
§ 371 (c)(1),
(2), (4) Date: Dec. 12, 2012

(87) PCT Pub. No.: WO2011/163391
PCT Pub. Date: Dec. 29, 2011

(65) Prior Publication Data
US 2013/0102877 A1    Apr. 25, 2013

Related U.S. Application Data

(60) Provisional application No. 61/357,361, filed on Jun. 22, 2010.

(51) Int. Cl.
*A61B 5/05*    (2006.01)
*G06T 7/00*    (2006.01)
(Continued)

(52) U.S. Cl.
CPC ............ *G06K 9/2054* (2013.01); *G06T 7/0081* (2013.01); *A61B 6/5217* (2013.01); *G06T 2207/10072* (2013.01); *G06T 7/0089* (2013.01); *A61B 6/03* (2013.01); *G06T 2207/20128* (2013.01); *A61B 5/055* (2013.01); *G01R 33/5608* (2013.01); *G06T 2207/30016* (2013.01)
USPC .............................. 600/410; 382/128; 703/11

(58) Field of Classification Search
USPC .......... 600/410, 411, 416; 382/128, 173, 190, 382/209, 224; 703/11
See application file for complete search history.

(56) References Cited

U.S. PATENT DOCUMENTS 6,633,686 B1    10/2003  Bakircioglu et al.
(Continued)

FOREIGN PATENT DOCUMENTS

WO    WO-2009/097612 A1    8/2009
WO    WO-2010005973 A2    1/2010

OTHER PUBLICATIONS

Seixas et al. Automatic Segmentation of Brain Structures Based on Anatomic Atlas. Seventh International Conference on Intelligent Systems Design and Applications. p. 329-334. Oct. 20, 2007.*
(Continued)

*Primary Examiner* — Parikha Mehta
(74) *Attorney, Agent, or Firm* — Venable LLP; Henry J. Daley; Trent B. Ostler

(57) ABSTRACT

A non-invasive imaging system, including an imaging scanner suitable to generate an imaging signal from a tissue region of a subject under observation, the tissue region having at least one anatomical substructure and more than one constituent tissue type; a signal processing system in communication with the imaging scanner to receive the imaging signal from the imaging scanner; and a data storage unit in communication with the signal processing system, wherein the data storage unit is configured to store a parcellation atlas comprising spatial information of the at least one substructure in the tissue region, wherein the signal processing system is adapted to: reconstruct an image of the tissue region based on the imaging signal; parcellate, based on the parcellation atlas, the at least one anatomical substructure in the image; segment the more than one constituent tissue types in the image; and automatically identify, in the image, a portion of the at least one anatomical substructure that correspond to one of the more than one constituent tissue type.

27 Claims, 8 Drawing Sheets

(51) Int. Cl.
*A61B 6/00* (2006.01)
*A61B 5/055* (2006.01)
*G06K 9/20* (2006.01)
*G01R 33/56* (2006.01)
*A61B 6/03* (2006.01)

(56) References Cited

U.S. PATENT DOCUMENTS

| | | | |
|---|---|---|---|
| 7,428,323 B2* | 9/2008 | Hillman | 382/128 |
| 2003/0139659 A1 | 7/2003 | Dale et al. | |
| 2006/0120584 A1* | 6/2006 | Hillman | 382/128 |
| 2007/0036402 A1* | 2/2007 | Cahill et al. | 382/128 |
| 2007/0167788 A1* | 7/2007 | Hartlep et al. | 600/447 |
| 2008/0188741 A1 | 8/2008 | Mallya et al. | |
| 2009/0226060 A1 | 9/2009 | Gering et al. | |
| 2010/0067761 A1* | 3/2010 | Jakobsson et al. | 382/131 |

OTHER PUBLICATIONS

Khan et al. FreeSurfer-initiated fully-automated subcortical brain segmentation in MRI using Large Deformation Diffeomorphic Metric Mapping. NeuroImage. 41:735-746. 2008.*

International Search Report and Written Opinion of PCT/US2011/04188.

* cited by examiner

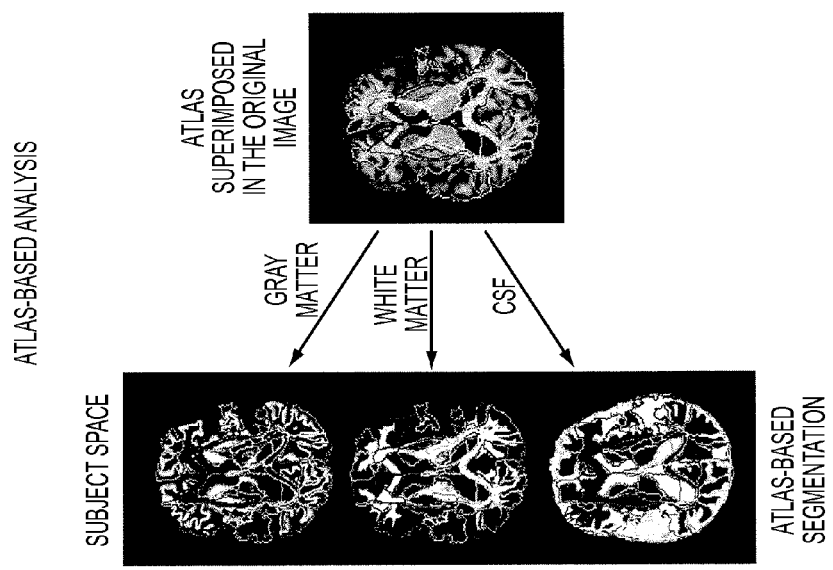
FIG. 3C
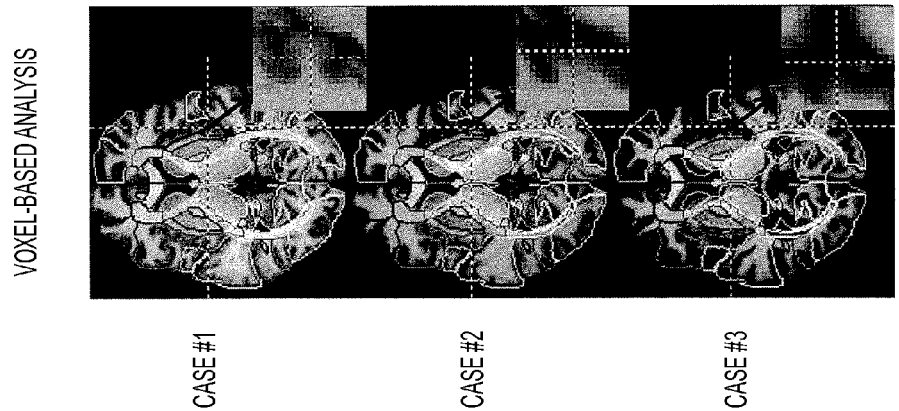

ATLAS-BASED ANALYSIS FOR IMAGE-BASED ANATOMIC AND FUNCTIONAL DATA OF ORGANISM

CROSS-REFERENCE OF RELATED APPLICATION

This application claims priority to U.S. Provisional Application No. 61/357,361 filed on Jun. 22, 2010, the entire contents of which are hereby incorporated by reference and is a U.S. national stage application under 35 U.S.C. 371 of PCT/US2011/041488 filed Jun. 22, 2011, the entire contents of which are incorporated herein by reference The U.S. Government has a paid-up license in this invention and the right in limited circumstances to require the patent owner to license others on reasonable terms as provided for by the terms of Grant No.: R01AG20012 and P41RR15241, awarded by the National Institutes of Health.

BACKGROUND

1. Field of Invention

The current invention relates to non-invasive imaging systems and methods, and more particularly to imaging systems and methods that provide computer assisted diagnosis of tissue abnormalities in human and animal subjects.

2. Discussion of Related Art

Conventional radiological diagnosis can be qualitative or subjective. Even though quantitative analyses may significantly improve our ability to detect and characterize abnormalities, currently almost no quantitative techniques can be accepted as a part of routine radiological diagnosis. This is partly due to difficulties in analyzing tissue regions based on radiological, such as Magnetic Resonance (MR), images. For example, a considerable amount of manual labor (typically 2-4 hours of tedious manual drawing) is required for high quality delineation of individual brains. Further delineation of the brain substructures would lead to even more manual labor. Automated programs for various types of tissue boundary delineation do exist but they can only provide approximate results. For automated image analysis, voxel-based analyses (VBAs) have been widely used. Initially, the shape of each brain may be transformed to that of an atlas brain. Once all brain images are transformed to the atlas, voxel-by-voxel analyses can be performed. In this type of analysis, each voxel is treated as an independent entity. This approach has not proven to be effective for clinical purposes and there is a need in the art for an automatic means of high quality delineation of tissue boundary that may improve detection and characterization of tissue abnormalities from current radiological images.

SUMMARY

An embodiment of the present invention provides a non-invasive imaging system, including an imaging scanner suitable to generate an imaging signal from a tissue region of a subject under observation, the tissue region having at least one anatomical substructure and more than one constituent tissue type; a signal processing system in communication with the imaging scanner to receive the imaging signal from the imaging scanner; and a data storage unit in communication with the signal processing system, wherein the data storage unit is configured to store a parcellation atlas comprising spatial information of the at least one substructure in the tissue region, wherein the signal processing system is adapted to: reconstruct an image of the tissue region based on the imaging signal; parcellate, based on the parcellation atlas, the at least one anatomical substructure in the image; segment the more than one constituent tissue types in the image; and automatically identify, in the image, a portion of the at least one anatomical substructure that correspond to one of the more than one constituent tissue type.

An embodiment of the present invention provides a workstation, including: a receiving engine adapted to receive an input image representing a tissue region of a subject, and a parcellation atlas comprising spatial information of at least one anatomical substructure in the tissue region; a normalizing engine constructed to provide a parcellated image by registering the parcellation atlas, via a transformation, to the input image; and a computing engine configured to automatically identify a portion of the at least one anatomical substructure, the portion corresponding to one constituent tissue type of the tissue region.

An embodiment of the present invention provides a method of analyzing an input image, including: receiving, from one of an imaging system, a workstation, or a data storage device, an input image representing a tissue region of a subject, wherein the input image comprises a plurality of image voxels, wherein the tissue region has a plurality of anatomical substructures and a plurality of constituent tissue types, and wherein at least one of the anatomical substructures comprises at least two constituent tissue types from the plurality of constituent tissue types; providing a parcellation atlas of the tissue region comprising spatial information of the anatomical substructures, wherein the parcellation atlas is from one of the first data storage device, or a second data storage device; generating a parcellated image by registering the parcellation atlas to the input image via a transformation, wherein the anatomical substructures of the tissue region are parcellated in the parcellated image; and providing a segmented parcellated image by identifying image voxels of one of the anatomical substructures in the parcellated image that correspond to one of the plurality of constituent tissue types.

BRIEF DESCRIPTION OF THE DRAWINGS

Further objectives and advantages will become apparent from a consideration of the description, drawings, and examples.

FIG. 3C shows a comparison of registration quality for voxel-based analysis and atlas-based analysis according to some embodiments of the present invention. Using the voxel-based analysis, the same coordinate could define the CSF, the cortex, or the white matter in different subjects, making the analysis inaccurate. Using the combination of atlas-based segmentation and tissue segmentation, each structure can be accurately defined in each subject.

DETAILED DESCRIPTION

Some embodiments of the current invention are discussed in detail below. In describing the embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
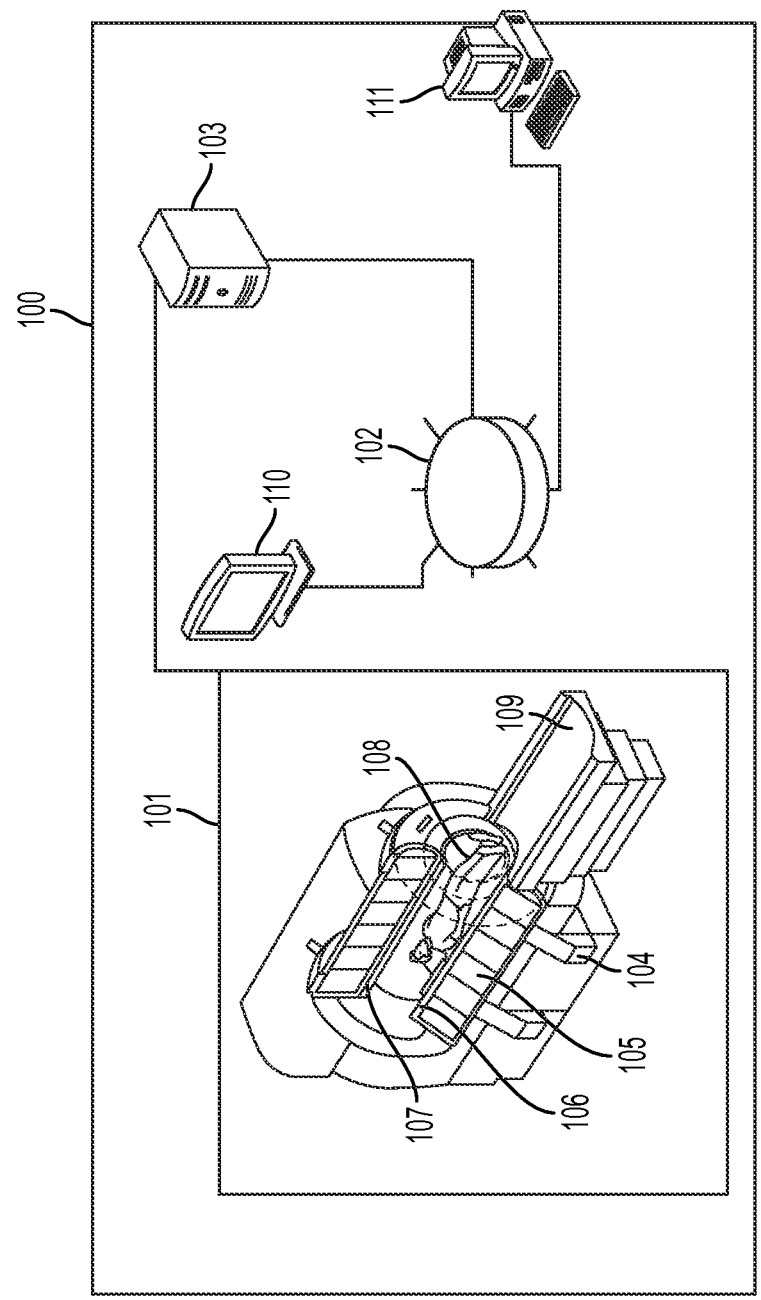
FIG. 1 is a schematic illustration of a non-invasive imaging system according to an embodiment of the current invention.

FIG. 1 is a schematic illustration of a non-invasive imaging system 100 according to some embodiments of the current invention. The non-invasive imaging system 100 includes an imaging scanner 101, a data storage unit 102, and a signal processing system 103. Imaging scanner 101 may be, but is not limited to, a magnetic resonance imaging (MRI) scanner, a computed tomography (CT) scanner, a positron emission tomography (PET) scanner, a single positron emission computed tomography (SPECT) scanner, or combinations thereof. For example, an MRI scanner may have a base 104 to support a main magnet 105 (providing a substantially uniform main magnetic field $B_0$ for a subject 108 under observation on scanner bed 109), a gradient system 106 (providing a perturbation of the main magnetic field $B_0$ to encode spatial information of the constituent water molecules of subject 108 under observation), and a radio-frequency (RF) coil system 107 (transmitting electromagnetic waves and receiving magnetic resonance signals from subject 108).

Data storage unit 102 may store atlas data corresponding to a tissue region of subject 108 under observation. The tissue region may be, for example, a brain, a heart, a liver, a muscle, and other intended organ of subject 108. The term "atlas" used herein does not necessarily require an actual material object, such as a three dimensional material object. It will be used generally to also refer to data or information that represents a spatial and geometrical configuration.

For example, data storage unit 102 may store a parcellation atlas of the tissue region including spatial information of the anatomical substructures of the tissue region. For example, the parcellation atlas may represent a human brain and may include information encoding location and shape of the various cortical substructures, etc. The parcellation atlas may be derived from, for example, a plurality of images from a subpopulation of subjects similar to subject 108. For example, the images can come from the same age group as subject 108 in some applications. This is because each age range may have different tissue shapes and contrasts. The parcellation atlas can be constructed to take into account variations between genders, races, or other subpopulations based on the potential application.

Data storage unit 102 may further store a segmenation atlas including, for example, spatial information of the constituent tissue types of the tissue region. For example, a brain tissue may have the constituent tissue types of the gray matter, the white matter, and the cerebrospinal fluid (CSF).

The plurality of images, used to construct the parcellation and segmentation atlas, may be, for example, MRI images, CT images, PET images, SPECT images, etc. The parcellation and segmentation atlas may incorporate information from images from at least one subject that is different from subject 108 under observation. The parcellation and segmentation atlas may incorporate information from images from a previous scan of subject 108 under observation. The parcellation and segmentation atlas may be derived from images of a variety of different contrasts, each favorably delineating, for example, certain substructures in the tissue region. For example, $T_1$-weighted magnetic resonance images suitable for the cortex and deep gray matter of the brain may be used. For example, $T_2$-weighted magnetic resonance images having higher contrasts for the ventricles of the brain may be used. For example, diffusion tensor images in which intra-white matter structures of the brain are best delineated may be used.

The parcellation atlas may include spatial information, such as, for example, shape information, location information, of the tissue region. The parcellation and segmentation atlas may further incorporate variability information associated with registering the spatial information to the soft tissue region in the images from a subpopulation of subject. Registering the spatial information of a atlas to the soft tissue region in an image from a subject to may involve warping or transforming (e.g., translation, scaling, deforming, etc.) the geometric information of the atlas to align with the soft tissue region in the image. Registering may also be referred to as normalizing.

The segmentation atlas may include spatial information, such as, for example, shape information, location information, transformation information when registering the segmentation atlas to the tissue region.

The term "atlas" include, but is not limited to the above examples.

Data storage unit 102 may be, for example, a hard disk drive, a network area storage (NAS) device, a redundant array of independent disks (RAID), a flash drive, an optical disk, a magnetic tape, a magneto-optical disk, etc. However, the data storage unit 102 is not limited to these particular examples. It can include other existing or future developed data storage devices without departing from the scope of the current invention.

Signal processing system 103 is in communication with imaging scanner 101 to receive imaging signals for forming images of subject 108. Signal processing system 103 may be partially or totally incorporated within a structure housing imaging scanner 101. Signal processing system 103 may be at least partially incorporated in a workstation that is structurally separate from and in communication with imaging scanner 101. Signal processing system 103 may be incorporated in a workstation that is structurally separate from and in communication with imaging scanner 101. Imaging signals received by signal processing system 103 may be associated with, for example, a magnetic resonance contrast parameter, such as, for example, a relaxation time $T_1$, a relaxation time $T_2$, an apparent diffusion coefficient, a property associated with the blood oxygenation level dependent (BOLD) effect, a property associated with the diffusion tensor, etc.

Signal processing system 103 is in communication with data storage unit 102. Signal processing system 103 is adapted: reconstruct an image of the tissue region based on the imaging signal from imaging scanner 101; parcellate, based on the parcellation atlas, an anatomical substructure in the reconstructed image showing the tissue region of the subject 108 under observation; segment the constituent tissue types of the tissue region in the reconstructed image; and automatically identify, in the reconstructed image, a portion of the anatomical substructure that corresponds to one the constituent tissue types.

Signal process system 103 may be further adapted to automatically diagnose whether a tissue abnormality is present in the tissue region of subject 108 by analyzing the portion of the anatomical substructure that corresponds to one of the constituent tissue types.

The automatically identified portion of the anatomical substructure may be visualized by superimposing the identified portion on the parcellated image at a viewing station 110 or a console station 111. Viewing station 110 or a console station 111 may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink jet printers, solid ink printers, dye-sublimation printers, and inkless printers such as thermal printers and ultraviolet (UV) printers, etc.

Figure 2A:
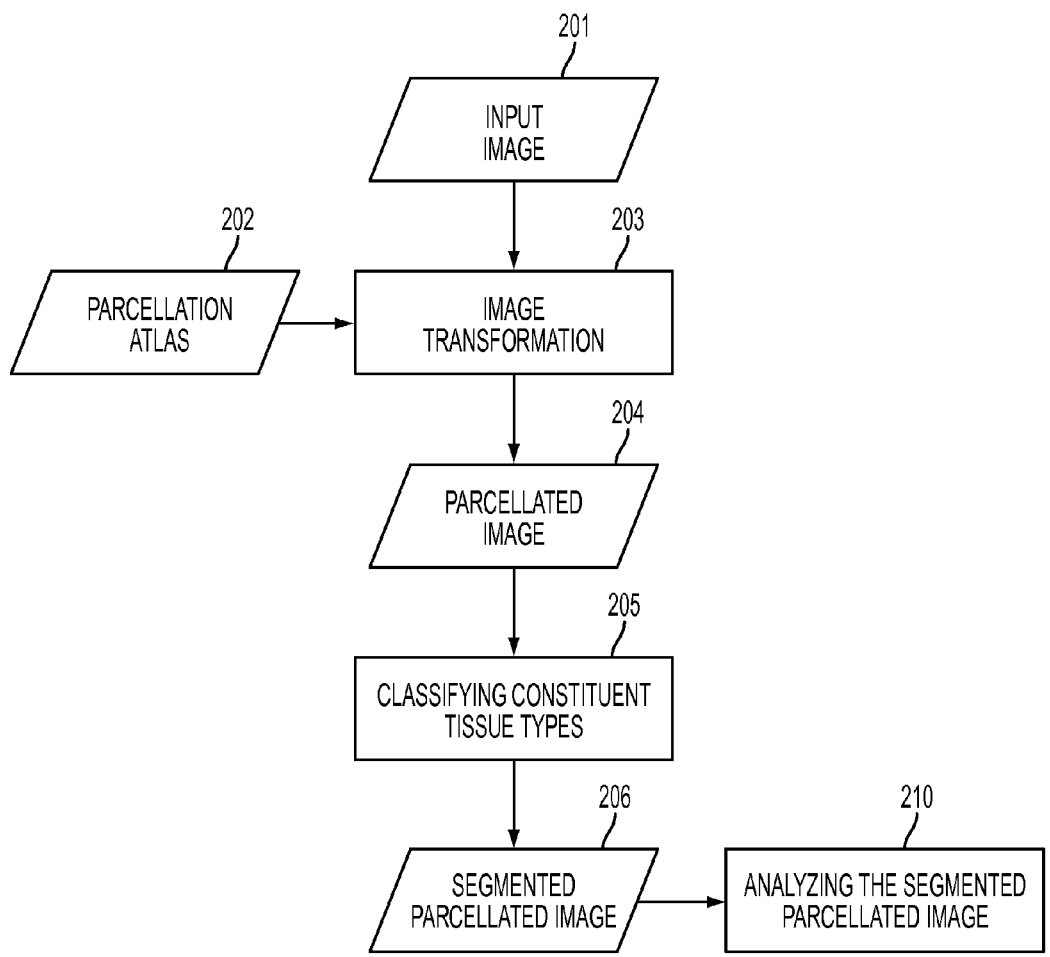
FIG. 2A shows a flow chart according to some embodiments of the current invention.

FIG. 2A shows a flow chart illustrating processes, implemented by one or more processors executing software code stored on one or more data storage devices, according to some embodiments of the present invention. The processors may be signal processors, computer processors, or combinations thereof. Example signal processors may include programmed field programmable gated array (FPGA) chips, programmed digital signal processing (DSP) chips, application specific integrated circuits (ASIC) chips, etc. Example computer processors may include single core or multi-core central processing units (CPU), single-core or multi-core graphic unit processing (GPU) chips, etc. In some embodiments of the current invention, the processes illustrated in FIG. 2A can be performed by data storage unit 102 and signal process unit 103.

Block 201 corresponds to an input image having more than one image voxel. Input image 201 corresponds to a tissue region having at least one anatomical substructure. Input image 201 may include more than one image showing the tissue region of a subject during a time course of observation. For example, the input image 201 may correspond to functional MRI (fMRI) images obtained over a period of observation time from patient 108. Input image 201 may be from an imaging system 101 or a data storage device 102. Input image 201 may be, for example, a Magnetic Resonance Imaging (MRI) image, a fMRI image, a Magnetic Resonance Spectroscopy (MRS) image, a Computed Tomography (CT) image, a Positron Emission Tomography (PET) image, a Single-photon Emission Computed Tomography (SPECT) image, etc. An MRI image may be a Diffusion Tensor Image (DTI). The MRI image may be based on a variety of contrast mechanisms, such as diffusion, perfusion, $T_1$ weighted, a $T_2$ weighted, etc.

Block 202 represents a parcellation atlas including spatial information of the tissue region, as discussed above. The parcellation atlas 202 may correspond to a finer spatial resolution than the input image 201.

In block 203, parcellation atlas 202 is normalized to input image 201. Registration may involve warping or transforming (e.g., translation, scaling, deforming, etc.) the soft tissue region in parcellation atlas 202 with shape of the same soft tissue region in input image 201. A transformation algorithm, called Large Deformation Diffeomorphic Metric Mapping (LDDMM) (Miller et al., 1993, Proc Natl Acad Sci, 90, 1194-11948; Joshi et al., 1995, Geometric methods in Applied Imaging, San Diego, Calif.; Granander and Miller, 1996, Statistical computing and graphics newsletter 7, 3-8), may be used during the registration. There can be several important technically attractive features of LDDMM. First, LDDMM is highly non-linear and can match the shapes of two brains. It can even transform a brain with severe atrophy. Second, LDDMM can achieve topology preservation. Topology preservation may be a very important feature when applying a morphing algorithm to a biological entity. For example, when morphing one face to another, if topology is not preserved, non-biological results can occur (e.g., two eyes become three eyes). Third the transformation can be reciprocal. Other transformation algorithms that can generate image transformation and preserve tissue topology can be used instead of LDDMM. In some cases, e.g. when only subtle changes in soft tissue regions are expected, the requirement of topology preserving can be waived.

Parcellated image 204 may be generated by image transformation block 203. Parcellated image 204 may be visualized by superimposing the transformed shape information of the soft tissue region from parcellation atlas 202 onto input image 201.

In block 205, the constituent tissue types of the soft tissue region are classified For a brain tissue, for example, the constituent tissue types may include gray matter (GM), white matter (WM), and cerebral-spinal fluid (CSF).

Figure 2B:
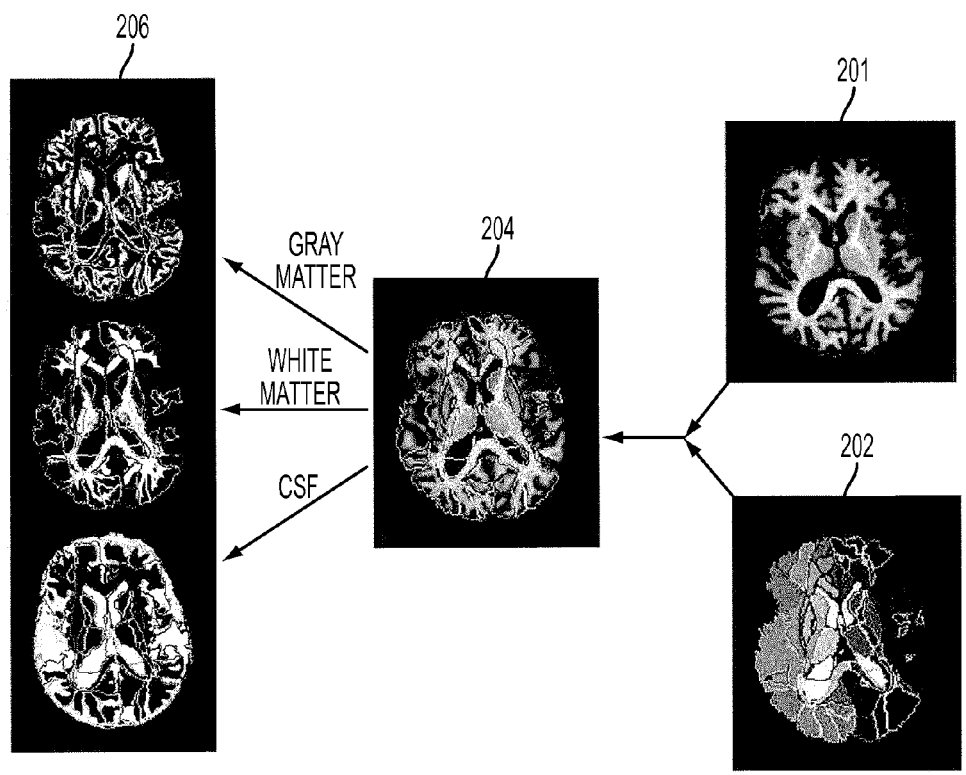
FIG. 2B shows an example processing flow according to some embodiments of the current invention.
Figure 2C:
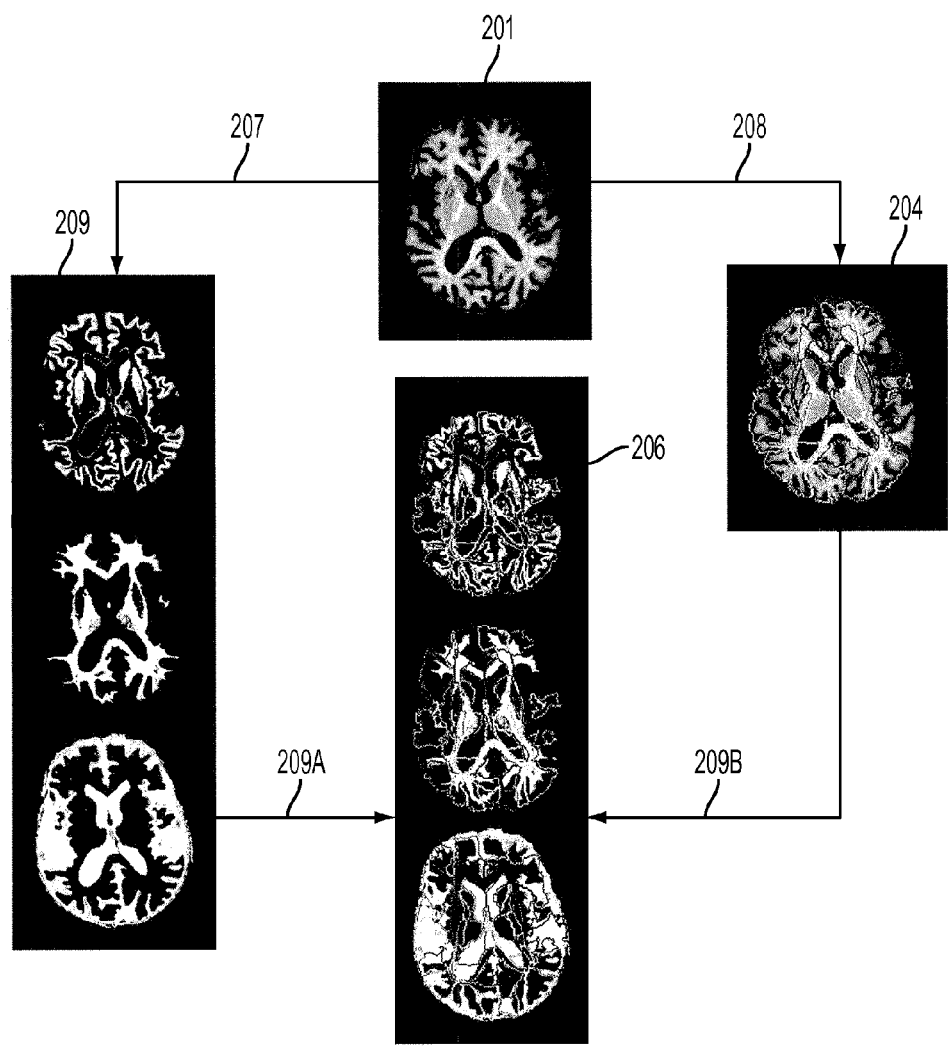
FIG. 2C shows an example flow of combining parcellation and segmentation according to some embodiments of the present invention.

Segmented parcellated image 206 may be generated by block 205. FIG. 2B shows three example segmented parcellated images 206, namely GM, WM, and CSF. In particular, the three example segmented parcellated images are provided by classifying the image voxels of the example parcellated image 204 according to the constituent tissue types of GM, WM, and CSF. The example parcellated image 204 is generated by transforming the example parcellation atlas 202 to the shape of the brain tissue in example input image 201. Alternatively, in FIG. 2C, a segmentation atlas is transformed, via link 207, to the brain tissue of the example input image 201 to generate example segmentation images 209 showing gray matter (top), white matter (middle), and cerebral spinal fluid (bottom). Meanwhile, an parcellation atlas may be transformed via link 208 to the brain tissue of example input image 201 to generate example parcellated image 204. Thereafter, example parceled image 204 and the three example segmentation images may be merged via links 209A and 209B to produce three segmented parcellated images 206, corresponding to gray matter (top), white matter (middle), and cerebral spinal fluid (bottom). Links 209A and 209B may correspond to a blending operation between a segmented image 206 and a parcellated image 204 on a voxel-by-voxel basis.

In block 210, the segmented parcellated image is analyzed to evaluate a tissue abnormality. The tissue abnormality may include, for example, a brain disease (e.g., including tissue atrophy such as primary progressive aphasia), a liver disease, a kidney disease, a muscle abnormality (such as, for example, muscle atrophy, muscle edema, muscle frailty, etc,) or a joint abnormality (such as, for example, rheumatoid arthritis, ostero-arthritis, etc.). The tissue anomaly may be an atrophy. For example, image voxels of one constituent tissue type from the same anatomical substructure may be combined for a quantitative analysis, including, for example, an average, a summation, a median. This combination may improve a quantitative index associated with the analysis, such as, for example, a sensitivity, a specificity, or reproducibility, as discussed below. This approach can also be used to analyze tissue anatomical and/or functional properties. For example, by applying the segmented parcellated image to Positron Emission Tomography (PET) scans, PET images can be quantified for each anatomical substructure. By measuring the time-dependent intensity changes of the voxels inside each anatomical substructure, functional MRI (fMRI) can be performed in a structure-specific manner with much higher signal-to-noise ratio. For resting-state fMRI, correlation between anatomical substructures can be studied instead of a large number of voxel-to-voxel correlation analysis. By applying each segmented parcellated anatomical substructure to a Magnetic Resonance Spectroscopy (MRS) data, a spectrum can be obtained for each anatomical substructure, enhancing the signal-to-noise ratio. This approach can be applied to the time-domain as well as the frequency-domain data. This approach also allows partial volume correction.

Figure 3A:
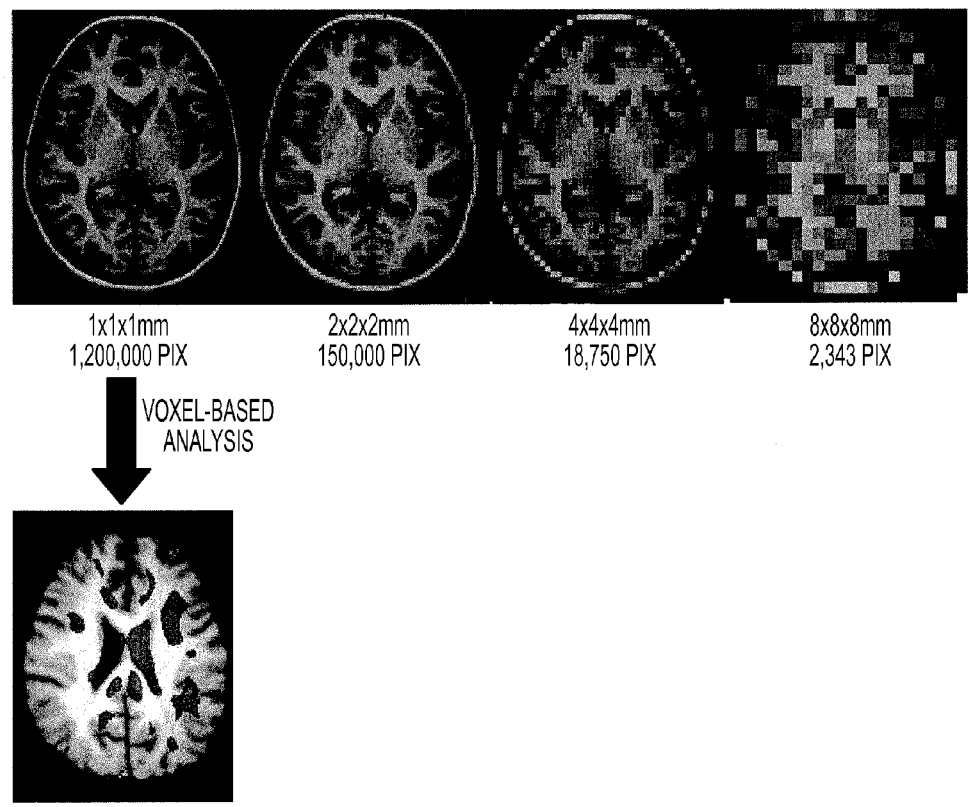
FIG. 3A shows an example dimension of voxel-based analysis. The voxel-based analysis deals with a large amount of voxels independently. Even with low-resolution imaging such as 8×8×8 mm, thousands of voxels are analyzed. The statistical averaging analysis of nearby voxels usually involves an isotropic spatial filtering that effectively reduces the spatial resolution. Clusters of voxels with statistical differences are in high-light.
Figure 3B:
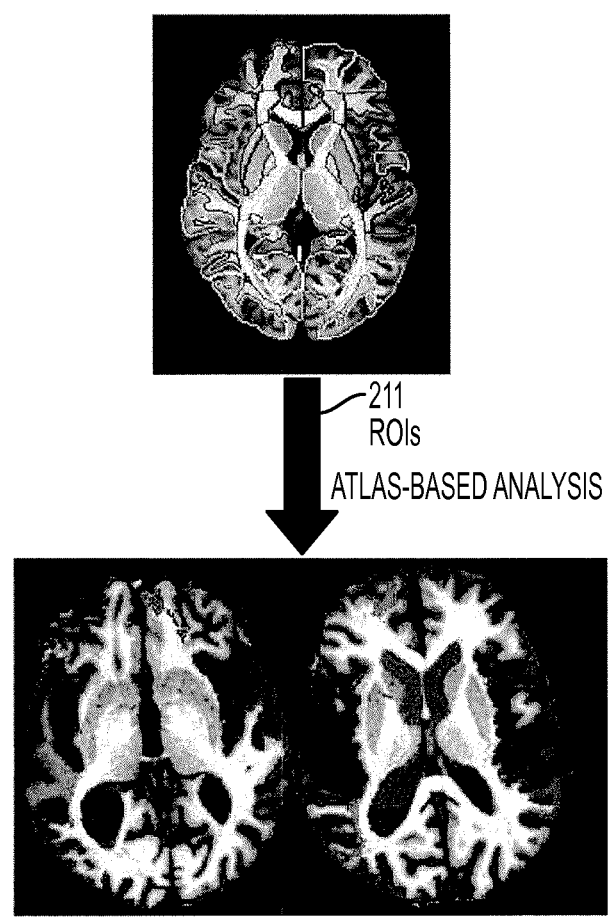
FIG. 3B shows an example dimension of atlas-based analysis according to some embodiments of the present invention. According to this atlas-based analysis, brain images are parcellated into each anatomical sub-structures. After statistical analysis, abnormality is detected in the structure-by-structure basis.

FIGS. 3A and 3B show example dimensions of a voxel-based analysis (VBA) and an atlas-based analysis (ABA), respectively. In particular, for an MRI image of a brain (1.2 L of volume) at a spatial resolution of 1×1×1 mm per image voxel, there are 1.2 million voxels corresponding to the brain tissue. The VBA performs quantification and statistical analysis for each of the 1.2 million voxels. The VBA approach is prone to the low signal-to-noise ratio (SNR) associated with each small image voxel. After multiple comparison tests for a large amount of images voxels (e.g. millions), statistical significance is still hard to achieve. One of the most widely used approaches to ameliorate this limitation is to effectively reduce the image resolution by applying a smoothing filter, as illustrated in FIG. 3A. For example, if the effective resolution is reduced to 8×8×8 mm, approximately 500 voxels are grouped together, leading to substantial enhancement of SNR. However, this leads to a severe loss of spatial anatomical information and tends to mix various constituent tissue types such as gray matter, white matter, and cerebrospinal fluid (CSF) of the brain tissue, as illustrated in FIG. 3A.

The atlas-based analysis, however, can group voxels in a structure-specific manner. For example, after the brain tissue has been parcellated into various anatomical structures as defined in the parcellation atlas, image voxels within an anatomical structure can be averaged. The averaging may also be performed for image voxels within the anatomical structure and corresponding to one constituent tissue type. For example, a brain tissue may be parcellated and segmented into regions, each corresponding to a constituent tissue type (e.g., gray matter, white matter, cerebrospinal fluid) in an anatomical substructure (e.g., a cortical substructure). There may be hundreds of such regions, instead of millions of image voxels. The corresponding image voxels of each region may be combined to boost the signal to noise ration of the region. The combination may be in the form of an averaging or summation. Thus, each brain image may then be treated as a vector with a dimension corresponding to the number of the regions. A diagnosis may be performed based on the vector.

Another potential advantage of the atlas-based analysis is that if combined with segmentation of different constituent tissue types, anatomically complex regions such as the cortex may be analyzed with improved quality, such as sensitivity, specificity, or reproducibility. Because of the large cross-subject variability, accurate registration of cortical areas may be unrealistic. FIG. 3C illustrates potential mis-registration within the cortical areas. As illustrated by the three cases on the left panel, the voxel as the same spatial location may correspond to any of the gray matter, the white matter, or the cerebral-spinal fluid. For fMRI, MR spectroscopy, PET, or morphological studies, mis-registration of the cortex would result in a mixture of the CSF and the white matter, leading to significant loss of sensitivity and specificity in subsequent medical diagnosis. For example, in cortical atrophy study, the cortex is likely to have atrophy while hypertrophy is expected for CSF. Mixture of these two constituent tissue types due to mis-registration is detrimental to subsequent medial diagnosis. In the atlas-based analysis, segmentation of each constituent tissue type can be performed accurately and the segmentation result may then be combined with the parcellated anatomical substructures, thereby substantially eliminating the mixtures of the constituent tissue types.

Furthermore, for MR spectroscopy and PET images, the spatial resolution of input images tend to be low (e.g., 5-10 mm). As a result, a increased level of partial volume effect is expected in which each image voxel contains a pronounced mixture of signal contribution from neighboring anatomical substructures. Applying a smooth filtering would only further degrade image resolution and should thus be avoided. In this scenario, the atlas-based analysis not only provides an improved way to group voxels, but also enables an estimate the amount of tissue mixture and a correction thereof. For example, based on co-registered high resolution anatomical MRI images (e.g., at a spatial resolution of 1×1×1 mm per image voxel), a high resolution parcellation atlas of the human brain may generated. This parcellation atlas may contain multiple anatomical substructures, including, for example, the ventricle, the caudate, and the internal capsule, all of which are adjacent each other. This parcellation atlas can be applied to low-resolution MR spectroscopy or PET images (e.g., at a spatial resolution of 10×10×10 mm per image voxle). For each 10×10×10 voxel, the ratio of the caudate, the ventricle, and the internal capsule can be calculated based on the corresponding set of image voxels in the high resolution parcellation atlas. For example, if a MR spectroscopy of the caudate is desired, it can be obtained by averaging the spectra of all voxels in the input image that correspond to the caudate, each weighted by the caudate ratio derived from the corresponding image voxels in the high resolution parcellation atlas. For example, one MRS voxel could be divided into two compartments, say, structure A and B with partial volume of $f_A$ and $f_B$. If the structure A contains 5 voxels, and each voxel has $f_A^i$ where i indicates pixel 1-5, a partial-volume-corrected spectrum for structure A can be obtain by $\Sigma f_A^i S^i$ where the $\Sigma$ sums over i and $S^i$ is the spectrum of pixel i.

Thus, the atlas-based analysis approach, as compared to a conventional voxel-based approach has been disclosed. An input image showing a soft tissue region of a subject may be parcellated into anatomical substructures of the soft tissue region by transforming a parcellation atlas to the shape of the soft tissue in the input image. The parcellated soft tissue region may be combined with the segmented constituent tissue types to provide a segmented parcellated image.

Figure 4:
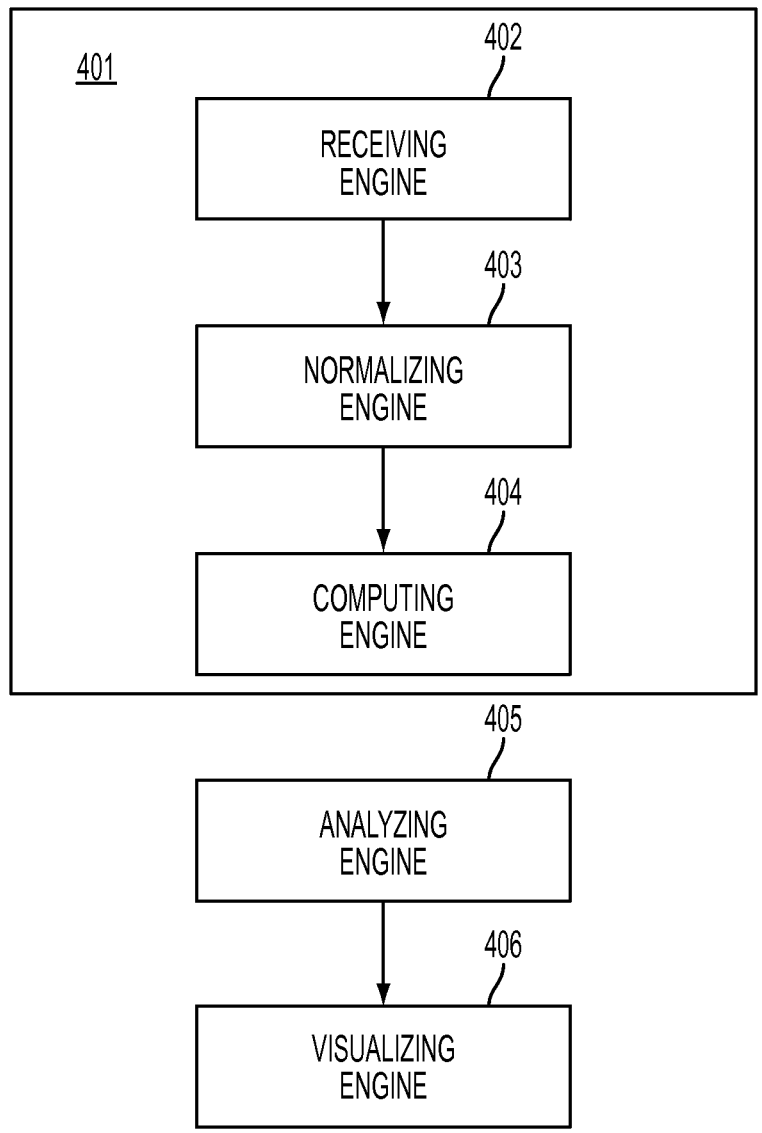
FIG. 4 shows a workstation according to an embodiment of the present invention.

FIG. 4 shows a workstation 401 according to some embodiments of the current invention. The workstation may include a receiving engine 402, a normalizing engine 403, a computing engine 404.

Receiving engine 402 may be adapted to receive an image data representing a soft tissue region of a subject, and a parcellation atlas comprising data encoding spatial information of at least one anatomical substructure in the soft tissue region. The received image data may have at least one contrast type that favorably delineates at least some of the substructure of the tissue region.

Normalizing engine 403 may be constructed to provide a parcellated image data by registering the parcellation atlas, via a transformation, to the input image data.

Computing engine 404 may be configured to automatically identify a portion of the at least one anatomical substructure that correspond to one of the constituent tissue types.

Workstation 401 may further comprise analyzing engine 405 configured to analyze the identified portion of the at least one anatomical substructure by combining image voxels corresponding to the identified portion.

Workstation 401 may further include a visualizing engine 406 to display the segmented parcellated input image. Visualizing engine 406 may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc.

Workstation 401 may be a computer with at least one central processing unit (CPU) and a plurality of memories. Workstation 401 may also be a dedicated processing machine with such devices as, for example, a field programmable gated array (FPGA), a digital signal processing (DSP) chip, a graphic processing unit (GPU), an application specific integrated circuit (ASIC), etc. Workstation 401 may also be incorporated in the imaging system 100.

The engines may be implemented by a computer with at least one processor and a plurality of memories. The processor may be, for example, one or more single-core or multi-core central processing unit (CPU), one or more single-core or multi-core graphic processing unit (GPU), etc. The computer may be a distributed computer comprising more than one processor connected via a network to divide the computation. Example networks may include, but is not limited to, an intranet, an extranet, the internet, or combinations thereof. Receiving engine 402, normalization engine 403, computing engine 404, and analyzing engine 405 may be implemented by, for example, a field programmable gated array (FPGA), a digital signal processing (DSP) chip, a graphic processing unit (GPU), an application specific integrated circuit (ASIC), etc.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A non-invasive imaging system, comprising:
   an imaging scanner configured to generate an imaging signal from a tissue region of a subject under observation, the tissue region having at least one anatomical substructure and more than one constituent tissue type;
   a signal processing system in communication with said imaging scanner configured to receive the imaging signal from said imaging scanner; and
   a data storage unit in communication with said signal processing system,
   wherein said data storage unit is configured to store a parcellation atlas comprising spatial information of said at least one anatomical substructure in the tissue region,
   wherein said signal processing system is adapted to:
      reconstruct an image of said tissue region based on said imaging signal;
      parcellate, based on the parcellation atlas, the at least one anatomical substructure in said image;
      segment the more than one constituent tissue type in said image to provide a plurality of segmented constituent tissue types, wherein the parcellation atlas includes at least one of imaging data (i) of the more than one constituent tissue type, (ii) of at least one of a plurality of imaging modalities and a plurality of imaging contrasts corresponding to one subject, and (iii) corresponding to a plurality of subjects;
      automatically identify, in said image, a portion of the at least one anatomical substructure that corresponds to one of the more than one constituent tissue type; and
      average all image voxels in the identified constituent tissue type to increase a signal-to-noise ratio of the automatically identified portion,
   wherein averaging the image voxels at least one of increases image resolution of said image and decreases scanning time from said imaging scanner, and
   wherein the at least one anatomical substructure is defined in one of the image modalities or imaging contrasts which has a higher signal-to-noise or resolution and applied to other image modalities or imaging contrasts.

2. The non-invasive imaging system according to claim 1, wherein said imaging scanner is a magnetic resonance imaging (MRI) scanner, a computed tomography (CT) imaging scanner, a positron emission tomography (PET) imaging scanner, a single positron emission computed tomography (SPECT) imaging scanner, or a combination thereof.

3. The non-invasive imaging system according to claim 1, wherein said imaging signal is capable of providing at least one contrast mechanism that delineates one of said more than one constituent tissue type of said tissue region.

4. The imaging system according to claim 1, wherein said signal processing system is further adapted to automatically diagnose whether a tissue abnormality is present in said tissue region of said subject by analyzing the portion of the at least one anatomical substructure that correspond to one of the more than one constituent tissue types.

5. The imaging system according to claim 1, further comprising:
   a viewing station or a console station configured to display the portion of the at least one anatomical substructure by superimposing said portion on said at least one anatomical substructure.

6. A workstation, comprising:
   a receiving engine adapted to receive an input image representing a tissue region of a subject, and
   a parcellation atlas comprising spatial information of at least one anatomical substructure in the tissue region;
   a normalizing engine configured to provide a parcellated image by registering the parcellation atlas, via a transformation, to the input image; and
   a computing engine configured to:
      automatically identify a portion of the at least one anatomical substructure, said portion corresponding to one constituent tissue type of said tissue region, wherein the parcellated atlas includes at least one of imaging data (i) of the more than one constituent tissue type, (ii) of at least one of a plurality of imaging modalities and a plurality of imaging contrasts corresponding to one subject, and (iii) corresponding to a plurality of subjects, and average all image voxels in the identified constituent tissue type to increase a signal-to-noise ratio of the automatically identified portion, wherein the at least one anatomical substructure is defined in one of the modalities or imaging contrasts and applied to other imaging modalities or imaging contrasts, and wherein averaging the image voxels at least one of increases image resolution of said image and decreases scanning time from said imaging scanner.

7. A workstation of claim 6, further comprising an analyzing engine configured to analyze said portion by combining image voxels corresponding to said portion.

8. The workstation according to claim 6, further comprising:

a visualizing engine adapted to display the parcellated image with said portion identified.

9. A method of analyzing an input image, comprising:

receiving, from one of an imaging system, a workstation, or a data storage device, an input image representing a tissue region of a subject, wherein the input image comprises a plurality of image voxels, wherein said tissue region has a plurality of anatomical substructures and a plurality of constituent tissue types, and wherein at least one of the plurality of anatomical substructures comprises at least two constituent tissue types from the plurality of constituent tissue types;

providing a parcellation atlas of said tissue region comprising spatial information of said anatomical substructures, wherein said parcellation atlas is from one of the first data storage device, or a second data storage device;

generating a parcellated image by registering said parcellation atlas to the input image via a transformation, wherein the anatomical substructures of said tissue region are parcellated in the parcellated image;

providing a segmented parcellated image by identifying image voxels of one of the anatomical substructures in the parcellated image that correspond to one of said plurality of constituent tissue types to provide a plurality of segmented constituent tissue types, wherein the parcellation atlas includes at least one of imaging data (i) of the more than one segmented constituent tissue types, (ii) of at least one of a plurality of imaging modalities and a plurality of imaging contrasts corresponding to one subject to generate the parcellation atlas, and (iii) corresponding to a plurality of subjects; and averaging all image voxels in the identified constituent tissue type to increase a signal-to-noise ratio of the segmented parcellated image, wherein averaging the image voxels at least one of increases image resolution of said image and decreases scanning time from said imaging scanner, and wherein the at least one anatomical substructure is defined in one of the image modalities or imaging contrasts which has a higher signal-to-noise or resolution and applied to other imaging modalities or imaging contrasts.

10. The method of claim 9, further comprising:

using the parcellated image or the segemented parcellated segmented image to improve a signal-to-noise ratio or an accuracy associated with an analysis of said input image.

11. The method of claim 9, further comprising:

analyzing said segmented parcellated image by grouping the image voxels of one of the anatomical substructures in the parcellated image that correspond to one of said plurality of constituent tissue types.

12. The method of claim 11, further comprising:

computing a quantity of the image voxels that correspond to one of said plurality of constituent tissue type and one of said anatomical substructures.

13. The method of claim 12, wherein said quantity is one of a mean, a sum, or a median.

14. The method of claim 12, further comprising:

automatically diagnosing a tissue abnormality of said tissue region based on said quantity.

15. The method of claim 14, wherein said tissue abnormality is one of a tissue atrophy, a stroke infarction, or a tumor.

16. The method of claim 14, wherein said tissue abnormality corresponds to an abnormality in one of a Magnetic Resonance Imaging (MRI) relaxation time change, a diffusion MRI parameter change, a Positron Emission Tomography (PET) image intensity, a Computed Tomography (CT) image intensity, or a Magnetic Resonance Spectroscopy (MRS) metabolite concentration.

17. The method of claim 11, further comprising:

increasing a quantitative index associated with said analyzing.

18. The method of claim 17, wherein said quantitative index is one of a sensitivity, a specificity, or a reproducibility.

19. The method of claim 9, wherein said identifying further comprises:

providing a segmentation atlas of said tissue region, said segmentation atlas comprising spatial information of said plurality of constituent tissue types; and segmenting the input image by registering said segmentation atlas of said tissue region, via a transformation, to said input image.

20. The method of claim 9, wherein said input image is one of a Magnetic Resonance Imaging (MRI) image, a functional MRI (fMRI) image, a Magnetic Resonance Spectroscopy (MRS) image, a Positron Emission Tomography (PET) image, or a Computed Tomography (CT) image.

21. The method of claim 9, wherein the parcellation atlas has a corresponding spatial resolution that is higher than the input image's spatial resolution.

22. The method of claim 21, further comprising:

compensating a partial volume effect in said input image by using the parcellation atlas to generate the parcellated image.

23. The method of claim 22, wherein said using the parcellation atlas further comprises:

estimating a weight of one of said plurality of anatomical substructures in each image voxel in the input image; and applying said weight to said parcellated image such that the parcellated image includes the weight.

24. The method of claim 9, further comprising:

using the segmented parcellated image to measure time-dependent image intensity changes in a functional MR1 (fMRI) study.

25. The method of claim 9, further comprising using the segmented parcellated image for a correlation analysis of a resting-state fMRI study.

26. The method of claim 9, wherein said transformation is a Large Deformation Diffeomorphic Metric Mapping (LDDMM).

27. A non-invasive imaging system, comprising:
an imaging scanner configured to generate an imaging signal from a tissue region of a subject under observation, the tissue region having at least one anatomical substructure and more than one constituent tissue type;
a signal processing system in communication with said imaging scanner configured to receive the imaging signal from said imaging scanner; and
a data storage unit in communication with said signal processing system,
wherein said data storage unit is configured to store a parcellation atlas comprising spatial information of said at least one anatomical substructure in the tissue region,
wherein said signal processing system is adapted to:
  reconstruct an image of said tissue region based on said imaging signal;
  parcellate, based on the parcellation atlas, the at least one anatomical substructure in said image to generate a parcellated image;
  segment the more than one constituent tissue type in said image to generate a segmented image;
  merge the parcellated image and the segmented image to generate a parcellated, segmented image; and
  automatically identify, in said parcellated, segmented image, a portion of the at least one anatomical substructure that corresponds to one of the more than one constituent tissue type.

* * * * *